United States Patent
Haruna et al.

(10) Patent No.: US 8,664,620 B2
(45) Date of Patent: Mar. 4, 2014

(54) PARTICLE BEAM ROTATIONAL IRRADIATION APPARATUS

(71) Applicant: Mitsubishi Electric Corporation, Chiyoda-ku (JP)

(72) Inventors: Nobuyuki Haruna, Chiyoda-ku (JP); Kazuo Yamamoto, Chiyoda-ku (JP); Takahisa Nagayama, Chiyoda-ku (JP)

(73) Assignee: Mitsubishi Electric Corporation, Chiyoda-Ku, Tokyo (JP)

(*) Notice: Subject to any disclaimer, the term of this patent is extended or adjusted under 35 U.S.C. 154(b) by 0 days.

(21) Appl. No.: 13/858,210

(22) Filed: Apr. 8, 2013

(65) Prior Publication Data

US 2013/0289330 A1    Oct. 31, 2013

(30) Foreign Application Priority Data

Apr. 27, 2012 (JP) .................................. 2012-102069
Dec. 27, 2012 (JP) .................................. 2012-284121

(51) Int. Cl.
*G21K 5/04* (2006.01)

(52) U.S. Cl.
USPC ............... 250/396 R; 250/397; 250/492.1; 250/492.3

(58) Field of Classification Search
USPC ............... 250/492.1, 492.3, 396 R, 397, 398, 250/396 ML; 315/500, 501, 502, 503, 504, 315/505; 600/1
See application file for complete search history.

(56) References Cited

U.S. PATENT DOCUMENTS

| 4,917,344 | A | 4/1990 | Prechter et al. | |
| 6,476,403 | B1 * | 11/2002 | Dolinskii et al. | 250/492.3 |
| 2010/0163755 | A1 | 7/2010 | Takeda et al. | |
| 2013/0187060 | A1 * | 7/2013 | Jongen | 250/396 R |

FOREIGN PATENT DOCUMENTS

| JP | 2000-140134 A | 5/2000 |
| JP | 2006-192297 A | 7/2006 |
| WO | WO 2008/026648 A1 | 3/2008 |

OTHER PUBLICATIONS

Jean Buon, "A statistical description of a particle beam subjected to a linear and coupled betatron motion", LAL/RT9603, Apr. 1996, pp. 1-10.

* cited by examiner

*Primary Examiner* — Nicole Ippolito

(74) *Attorney, Agent, or Firm* — Buchanan Ingersoll & Rooney PC

(57) ABSTRACT

The particle beam rotational irradiation apparatus is provided with an irradiation nozzle that irradiates a charged particle beam, a beam transport unit that transports the charged particle beam to the irradiation nozzle, and a rotating unit that can rotate around the isocenter; the particle beam rotational irradiation apparatus is characterized in that the beam transport unit has three or more bending electromagnets and in that the bending electromagnets are arranged in such a way that in the case where as a pair of bending planes, any two of the bending planes of the bending electromagnets are selected, the two bending planes of at least one pair of bending planes are not on the same plane, not parallel with each other, and not perpendicular to each other.

10 Claims, 8 Drawing Sheets

PARTICLE BEAM ROTATIONAL IRRADIATION APPARATUS

BACKGROUND OF THE INVENTION

1. Field of the Invention

The present invention relates to a particle beam rotational irradiation apparatus (a rotating gantry), the objective of which is to irradiate a charged particle, accelerated by an accelerator, from an arbitrary angle direction.

2. Description of the Related Art

Charged particles are circulated and accelerated in a circular accelerator such as a synchrotron and then the charged particles (mainly protons or carbon ions), which have been accelerated to gain high energy, are extracted from the circulation orbit; the charged particles (referred to also as charged particle beam or particle beam) are utilized in a physics experiment or in a particle beam therapy such as a cancer treatment, in which the charged particles are transported through a beam transport line and irradiated onto a desired subject. In general, in a cancer treatment utilizing accelerated charged particles, i.e., in a so-called particle beam therapy, the irradiation directions are changed for the purpose of averting the charged particles from major organs during the treatment or preventing normal tissues from being damaged. As one of the means of changing the irradiation directions of the charged particle beams, a particle beam rotational irradiation apparatus (rotating gantry) is commonly utilized in which an irradiation nozzle is mounted in a structural member that rotates around a patient and the charged particles can be irradiated from a desired angle.

For example, in a rotating gantry (referred to simply as a gantry, as may be necessary) disclosed in Patent Document 1, a charged particle beam is once bended by two bending electromagnets in such a way that the beam transport line becomes perpendicular to the rotation axis of the rotating gantry; then, the charged particle beam is introduced by bending the charged particle beam again by use of two bending electromagnets in such a way that on a plane perpendicular to the center axis of the gantry, the charged particle beam is directed to the isocenter (the intersection point of the gantry rotation axis with the beam axis, which is the reference of the irradiation target). This kind of beam transport line makes the length of the rotating gantry shortest with respect to the rotation-axis direction; therefore, as a result, it is made possible to install a rotating gantry in a small area. In some cases, a rotating gantry provided with this kind of beam transport line is referred to as a corkscrew-type gantry. In addition, the bending electromagnets are two-pole electromagnets provided with two magnetic poles.

It is another characteristic of a corkscrew-type gantry that at least four bending electromagnets are required. The reason for that will be explained below. In general, the momentum of a charged particle beam extracted from a circular accelerator does not have a certain single value but has spread around the center value. The value obtained through dividing a deviation amount from the center value by the center value is referred to as a momentum spread. When a charged particle beam having a momentum spread passes through the bending electromagnet, the bending angle thereof changes depending on the momentum (it might be considered as energy or a velocity) of the charged particle beam; therefore, when the spread is left as it is, the width (referred to as a beam size, hereinafter) of particle distribution at the isocenter may become large.

Letting $p_0$ and $\Delta p/p_0$ denote the momentum (center momentum) of a particle having the center momentum at a given position and the momentum spread, respectively, the deviation (the spread of a beam width due to the momentum spread) $\Delta x$ from the center orbit, which is the orbit of the particle having the center momentum $p_0$, is given as the equation (1) by use of a dispersion function $\eta$ that characterized the effect of the momentum spread at the given position. The dispersion function $\eta$ is a function of the position of a beam transport line.

$$\Delta x = \eta \times \Delta p/p_0 \quad (1)$$

In general, as an element for causing the dispersion function $\eta$, a bending electromagnet is utilized; when the dispersion function $\eta$ once becomes a value other than "0", it is required to cancel $\eta$ and $\eta'$ by use of at least another bending electromagnet and quadrupole electromagnets. Here, $\eta'$ denotes the differentiation in the beam traveling direction (s direction, s axis). Because an actual irradiation site is not a point like an isocenter and has a width in the depth direction, it is required to nullify the gradient $\eta'$ of the dispersion function $\eta$. A dynamic change of a momentum spread makes the charged particle beam look like moving. In general, it is required, in a rotating gantry, that the dispersion function $\eta$ is diminished at the isocenter to the extent that its contribution to the spread of a beam width can be allowed, in order to prevent the beam width from changing or moving at the isocenter.

In the case of the corkscrew-type gantry disclosed in Patent Document 1, two bending electromagnets at the upstream side are situated on the same plane; therefore, the dispersion function $\eta$ caused by the first bending electromagnet is nullified by the other bending electromagnet that has the bending plane thereof on the same plane. In this situation, a plurality of quadrupole electromagnets provided between the bending electromagnets are utilized for changing the s-direction gradient ($\eta'$) of the dispersion function $\eta$ in addition to focusing or defocusing a charged particle beam. The bending planes of two bending electromagnets at the downstream side differ by 90 degrees from those of the two bending electromagnets at the upstream side; as is the case with the upstream side, $\eta$ and $\eta'$ are nullified by the two electromagnets and a plurality of quadrupole electromagnets provided between the bending electromagnets. In general, in the designing of the beam transport line between a circular accelerator and a rotating gantry or in the designing of the beam transport line of a rotation gantry, there exists a type in which all bending electromagnets are arranged in a single bending direction and nullify $\eta$ and $\eta'$, which are caused in only a single direction, in collaboration with quadrupole electromagnets, or a type, as disclosed in Patent Document 1, in which a plurality of bending electromagnets are arranged in such a way that although respective $\eta$ and $\eta'$ are caused in both the x direction and the y direction, 90-degree-different bending planes makes the x-direction dispersion function $\eta$ and the y-direction dispersion function $\eta$ not couple with each other, i.e., the x-direction dispersion function $\eta$ and the y-direction dispersion function $\eta$ are independent in the respective directions thereof.

Next, a gantry in which $\eta$ and $\eta'$ are caused in only a single direction will be explained. In the rotating gantry disclosed in Patent Document 2, three bending electromagnets lead a charged particle beam to the isocenter. Because three bending electromagnets are provided, the dispersion function is nullified in only one direction in the designing of the beam transport line of the rotating gantry, unless the coupling is not utilized; thus, the bending planes of a charged particle beam is made to be a single and the same by the three bending electromagnets. Accordingly, the beam transport line of the rotating gantry disclosed in Patent Document 2 becomes longer in the beam-rotation-axis direction than that of the corkscrew-type gantry; as a result, the area where the rotating gantry is installed becomes wider.

In recent years, it has been required to raise the throughput of particle beam therapy, as particle beam therapy has become widespread. In particle beam therapy, before a charged particle beam is irradiated onto a patient, a person who offers assistance in the therapy, for example, a radiologist approaches a patient platform or an irradiation nozzle and fixes the patient body or adjusts irradiation-system apparatuses that are to be mounted on an irradiation nozzle. In this situation, in order to shorten the time for the adjustment, i.e., in order to raise the throughput of the therapy, the easiness degree of the foregoing work at the vicinity of the irradiation nozzle is important. An example of rotating gantry that facilitates the work at the vicinity of the irradiation nozzle is disclosed, for example, in Patent Document 3. By constructing a rotating gantry (referred to as an open type, hereinafter) in such a way that as illustrated in FIG. 6 of Patent Document 3, the front end of the irradiation apparatus (irradiation nozzle) protrudes toward the irradiation room, the work to be performed in the vicinity of the irradiation nozzle can be facilitated. Moving body tracking, in which high-accuracy irradiation is performed while the motion of an organ undergoing irradiation or the motion of a body caused by respiration is monitored in real time, has also been attracting attention; therefore, it is desired to secure a sufficient space for arranging monitoring apparatuses in the vicinity of the irradiation nozzle.

PRIOR ART REFERENCE

Patent Document

[Patent Document 1] U.S. Pat. No. 4,917,344 (FIGS. 1a and 1b)
[Patent Document 2] International Publication No. WO2008/026648A1 (FIG. 1)
[Patent Document 3] Japanese Patent Application Laid-Open No. 2006-192297 (FIG. 6)
[Patent Document 4] Japanese Patent Application Laid-Open No. 2000-140134 (FIGS. 1, 2, and 6)

As the rotating gantry disclosed in Patent Document 2 can be realized to construct, the open-type rotating gantry disclosed in Patent Document 3 can be realized to construct, because three bending electromagnets lead a charged particle beam to the isocenter. However, the rotating gantry (corkscrew-type gantry) disclosed in Patent Document 1 is a type that requires a small installation area; thus, it is difficult to apply an open-type structure to this kind of rotating gantry. The reason for that will be explained with reference to the drawings of Patent Document 4.

The rotating gantry disclosed in Patent Document 4 is a corkscrew-type gantry, as is the case in Patent Document 1. FIGS. 1 and 2 of Patent Document 4 illustrate a left-side view and an elevation view of a rotating gantry, respectively; FIG. 6 of Patent Document 4 illustrates a left-side view of a rotating frame in which an isocenter $C_I$ is shown. The rotating gantry disclosed in Patent Document 4 is a type in which the irradiation nozzle (Reference Numeral 15 of Patent Document 4) is provided inside the rotating frame (Reference Numeral 2 of Patent Document 4) and the isocenter $C_I$ is situated in the rotating frame. The rotating gantry disclosed in Patent Document 4 is different from a rotating gantry in which as is the case in Patent Document 3, the irradiation nozzle (Reference Numeral 8 of Patent Document 3) is provided outside the rotating frame (Reference Numeral 1 of Patent Document 3).

In the corkscrew-type gantry disclosed in Patent Document 1 or 4, two bending electromagnets at the downstream side are arranged in a row on a plane perpendicular to the rotation axis so that the installation area is diminished; therefore, in order to realize an open-type rotating gantry in which an irradiation nozzle to be disposed under the last bending electromagnet is provided in the treatment room, not only the irradiation nozzle and the downstreammost bending electromagnet but also another bending electromagnet, which forms a pair with the downstreammost bending electromagnet, are made to protrude into the treatment room. Because it is difficult to support the two bending electromagnets and the irradiation nozzle by the frame of the rotating gantry, it is difficult to realize a corkscrew-type gantry having an open-type rotating gantry. Accordingly, as is the case in the rotating gantry disclosed in Patent Document 2, in the corkscrew-type gantry disclose in Patent Document 1 or 4, it is inevitable to perform irradiation onto a patient in a hole-shaped narrow space (inner chamber); therefore, the work to be performed in the vicinity of the irradiation nozzle becomes hard. Moreover, even if the two bending electromagnets and the irradiation nozzle can be arranged in the treatment room, the space for disposing monitoring apparatuses around the irradiation nozzle or the space that facilitates the work to be performed in the vicinity of the irradiation nozzle cannot sufficiently be secured.

To date, such a corkscrew-type gantry as disclosed in Patent Document 1 has been utilized in order to cancel the momentum-spread dependence of a beam position at the isocenter. In order to realize an open-type rotating gantry, it is required that as is the case with a rotating gantry that requires a large installation area, i.e., as is the case with the rotating gantry disclosed in Patent Document 2 or 3, the bending electromagnets are arranged in such a way that the bending planes of all the bending electromagnets are the same; therefore, there has been a problem that it is difficult to realize a gantry that requires a small installation area.

In an open-type rotating gantry, as disclosed in Patent Document 3, that is suitable to raise the throughput of particle beam therapy, the irradiation nozzle is made to protrude into the irradiation room; therefore, the patient-positioning work performed in the vicinity of the irradiation nozzle can be facilitated. However, because the bending electromagnets are arranged in such a way that the bending planes of all the bending electromagnets are the same, there has been a problem that the installation area becomes large.

SUMMARY OF THE INVENTION

The objective of the present invention is to realize a particle beam rotational irradiation apparatus that can raise the throughput of particle beam therapy and can be downsized.

A particle beam rotational irradiation apparatus according to the present invention is provided with an irradiation nozzle that irradiates a charged particle beam, a beam transport unit that transports the charged particle beam to the irradiation nozzle, and a rotating unit that can rotate around the isocenter; the particle beam rotational irradiation apparatus is characterized in that the beam transport unit has three or more bending electromagnets and in that the bending electromagnets are arranged in such a way that in the case where as a pair of bending planes, any two of the bending planes of the bending electromagnets are selected, the two bending planes of at least one pair of bending planes are not on the same plane, not parallel with each other, and not perpendicular to each other.

In a particle beam rotational irradiation apparatus according to the present invention, the bending electromagnets are arranged in such a way that in the case where as a pair of bending planes, any two of the bending planes of the bending electromagnets are selected, the two bending planes of at least one pair of bending planes are not on the same plane, not parallel with each other, and not perpendicular to each other; therefore, the working space for performing patient positioning work can be widened even in the case of a small-size particle beam rotational irradiation apparatus and hence the throughput of particle beam therapy can be improved.

The foregoing and other object, features, aspects, and advantages of the present invention will become more apparent from the following detailed description of the present invention when taken in conjunction with the accompanying drawings.

DETAILED DESCRIPTION OF THE PREFERRED EMBODIMENTS

Embodiment 1

Figure 1:
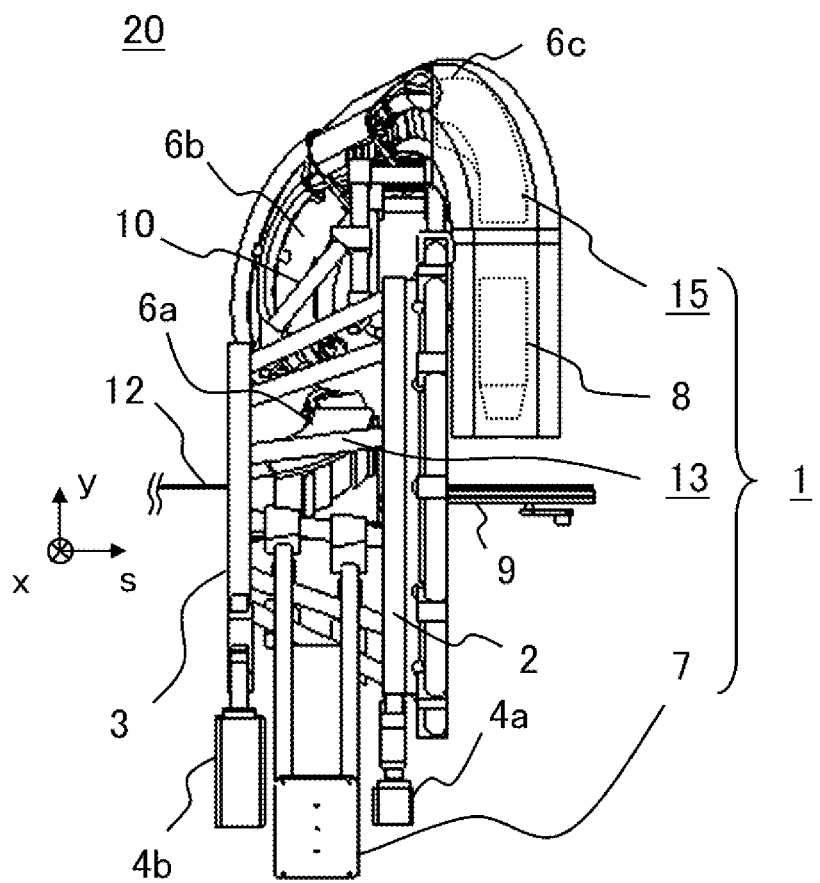
FIG. 1 is a side view illustrating a particle beam rotational irradiation apparatus according to Embodiment 1 of the present invention.
Figure 2:
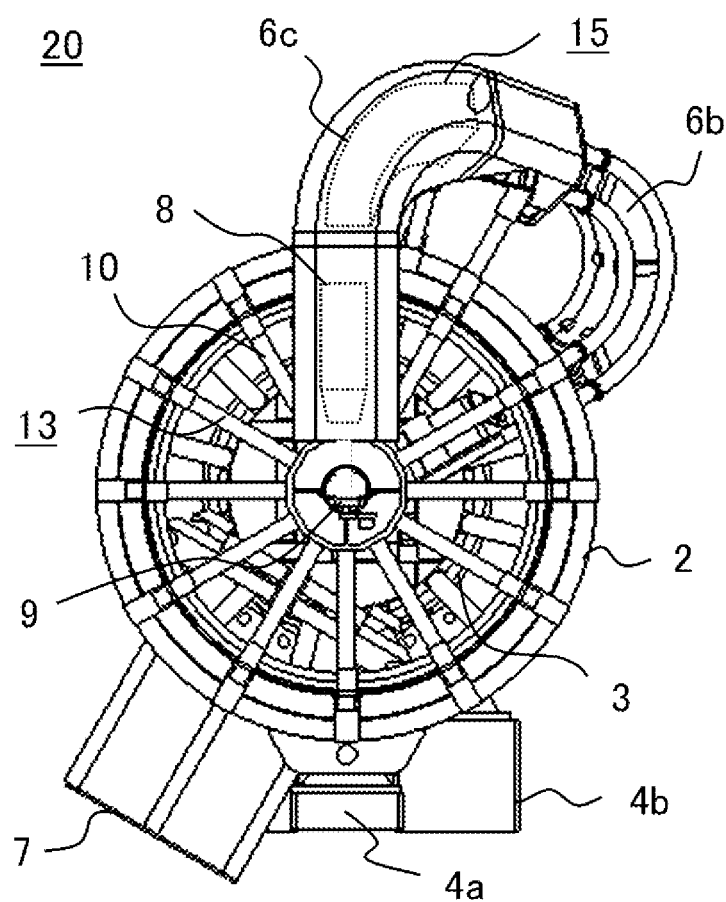
FIG. 2 is an elevation view illustrating the particle beam rotational irradiation apparatus in FIG. 1.
Figure 3:
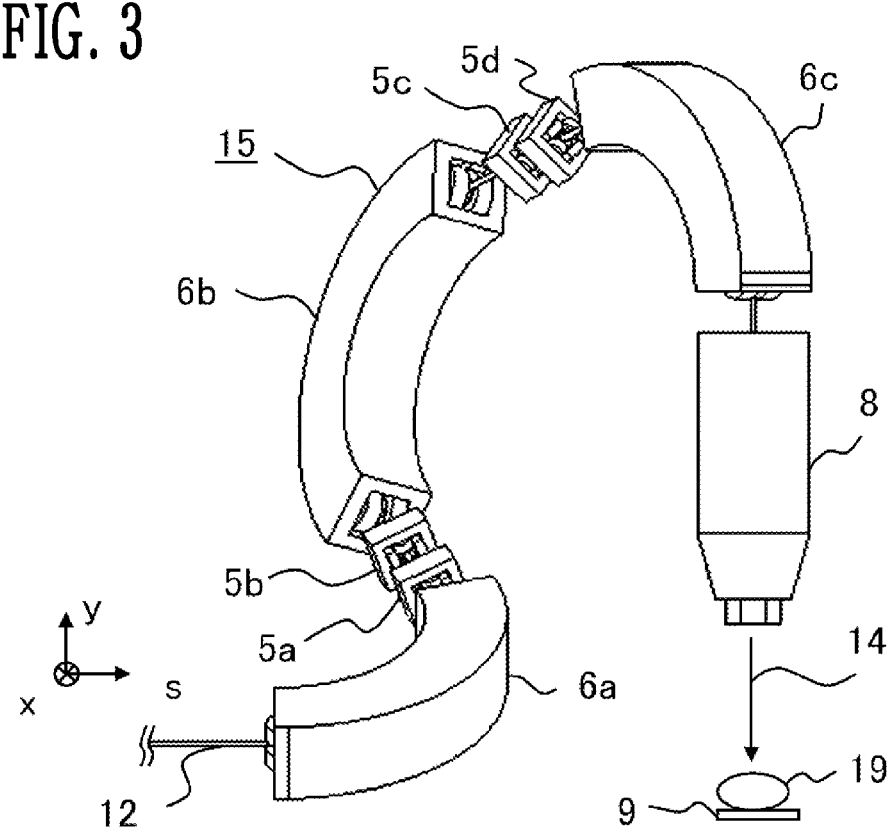
FIG. 3 is a view illustrating the beam transport unit in FIG. 1.

FIG. 1 is a side view illustrating a particle beam rotational irradiation apparatus according to Embodiment 1 of the present invention; FIG. 2 is an elevation view illustrating a particle beam rotational irradiation apparatus according to Embodiment 1 of the present invention. FIG. 3 is a view illustrating a beam transport unit according to Embodiment 1 of the present invention. A particle beam rotational irradiation apparatus 20 is provided with a rotating unit 1 that rotates around the isocenter, supporting bases 4a and 4b that support the rotating unit 1, and a rotation-driving system (unillustrated) that makes the rotating unit 1 rotate. The rotating unit 1 is provided with a body unit 13, a beam transport unit 15 that transports a charged particle beam 14, an irradiation nozzle 8 (refer to FIG. 3) that irradiates the charged particle beam 14 onto an irradiation subject 19, and a weight 7 whose weight is balanced with that of the beam transport unit 15. The body unit 13 has a front ring 2, a rear ring (bearing) 3, and a plurality of supporting members 10; the body unit 13 is a structure that supports the beam transport unit 15.

FIG. 3 is a view of the beam transport unit 15 and the irradiation nozzle 8 taken for the sake of easier understanding of the arrangement, of bending electromagnets 6a, 6b, and 6c, that characterize the present invention. In FIGS. 1 through 3, the bases are omitted. The beam transport unit 15 has a beam transport duct 12, three bending electromagnets 6a, 6b, and 6c, and four quadrupole electromagnets 5a, 5b, 5c, and 5d. The beam transport unit 15 does not include a Wobbler electromagnet and a scanning electromagnet in the irradiation nozzle 8. As the reference numerals of the bending electromagnets, "6" is collectively utilized; however, in the case where the bending electromagnets are separately explained, "6a", "6b", and "6c" are utilized. As the reference numerals of the quadrupole electromagnets, "5" is collectively utilized; however, in the case where the quadrupole electromagnets are separately explained, "5a", "5b", "5c", and "5d" are utilized. As the reference numerals of the supporting bases, "4" is collectively utilized; however, in the case where the supporting bases are separately explained, "4a" and "4b" are utilized. The bending electromagnet 6 and the quadrupole electromagnets 5 are beam transport electromagnets.

The beam transport duct 12 is a vacuum duct or the like that generates a vacuum inside the apparatus. A charged particle beam 14, accelerated by a circular accelerator (synchrotron), passes through the inside of the beam transport duct 12 in which a vacuum has been generated. The bending electromagnets 6a, 6b, and 6c each bend the charged particle beam 14 toward predetermined directions. The quadrupole electromagnets 5a, 5b, 5c, and 5d each focus or defocus the charged particle beam 14 and change the beam-path-direction gradient $\eta'$ of the dispersion function $\eta$ of the charged particle beam 14 so as to adjust the beam width to be within a tolerance range.

The characteristic of the present invention is that the three bending electromagnets 6a, 6b, and 6c are arranged in such a way that the two bending planes of at least one pair among three pairs of the bending planes thereof are not on the same plane, not parallel with each other, and not perpendicular to each other. In other words, it suggests that when the bending planes of the three bending electromagnets 6a, 6b, and 6c are extended and crossed one another, the angle between the two bending planes of at least one pair among three pairs of the bending planes thereof is between 0 degree and 90 degrees. Moreover, it suggests that the angle between the bending magnetic fields (double-pole magnetic fields) of at least one pair among three pairs of the bending magnetic fields of the three bending electromagnets 6a, 6b, and 6c is between 0 degree and 90 degrees when the direction of the magnetic field is viewed on the xy plane that is perpendicular to the beam traveling direction. Accordingly, the respective motions of a particle, in the x direction and the y direction, that has undergone the magnetic fields of the bending electromagnet 6 and the quadrupole electromagnet 5 are not independent from each other; instead, they are coupled with each other. Here, the x axis and y axis are each perpendicular to the beam traveling direction (s direction, s axis). Because the particle beam rotational irradiation apparatus 20 rotates, the x axis and the y axis, explained herein, are defined to be one axis for the direction of the double-pole magnetic field between the magnetic poles at the inlet side of the bending electromagnet 6 at the upstreammost side, i.e., the first bending electromagnet 6a at a given rotation angle, and an another axis for the direction perpendicular to the one axis, respectively.

In general, in such a particle beam rotational irradiation apparatus (rotating gantry) as disclosed in Patent Document 2 or 3, the bending electromagnets are arranged in such a way that the bending planes thereof are on the same plane, so that there is utilized the effect that the bending electromagnets and quadrupole electromagnets change the dispersion function η and the beam-path-direction gradient η' of the dispersion function η. In a particle beam rotational irradiation apparatus (rotating gantry), by utilizing this effect, the dispersion function η is nullified or diminished to the extent that its contribution is sufficiently small so as to cancel the beam size dependence on the momentum spread at the isocenter. In this situation, the bending electromagnet can cause η; however, the quadrupole electromagnet only changes the gradient η'. The only way to keep the beam size dependence at "zero", i.e., "η=0 and η'=0" is to change the gradient η' by use of the quadrupole electromagnet and then cause an opposite-sign η by use of the bending electromagnet. By bending a particle beam by α degree and then bending it by −α degree on the same plane, the mode "η=0 and η'=0" can be realized only by the bending electromagnets. However, this method may cause η to become so large during the transport of a charged particle beam that the beam hits the duct. In the case of such a corkscrew-type gantry as disclosed in Patent Document 1 or 4, respective momentum spread dependences are caused in the x direction and the y direction. That is to say, the mode in which ηx≠0 and ηy≠0 takes place. However, in the case where a corkscrew-type gantry is provided with two bending electromagnets for bending a beam on a plane including the s axis and the x axis, two bending electromagnets for bending a beam on a plane including the s axis and the y axis, and a quadrupole electromagnet between the bending electromagnets, the mode in which ηx=0, ηy=0, ηx'=0, and ηy'=0 can be obtained.

As a result, not only the respective momentum-spread dependences of a beam width in the x direction and the y direction can be cancelled at the isocenter, but also the respective gradients η' (ηx', ηy') in the x direction and the y direction can be nullified at the isocenter.

In the case where bending electromagnets are arranged in the same manner as Embodiment 1, i.e., in the case where the three bending electromagnets 6a, 6b, and 6c are arranged in such a way that the two bending planes of at least one pair among three pairs of the bending planes thereof are not on the same plane, not parallel with each other, and not perpendicular to each other, the respective motions of a particle in the x direction and the y direction are coupled with each other. Thus, the respective bending planes of the bending electromagnets 6a, 6b, and 6c do not separately nullify (or sufficiently diminish) the dispersion functions; instead, by utilizing the coupling of the respective motions of a particle in the x direction and the y direction, both the x-direction dispersion function ηx and the y-direction dispersion function ηy and both the x-direction gradient ηx' and the y-direction gradient ηy' of the x-direction dispersion function and the y-direction dispersion function can eventually be nullified or sufficiently be diminished at the isocenter. This method will be explained below by use of a transfer matrix utilized in beam designing calculation.

When attention is paid to a single particle in a charged particle beam, the transfer matrix can be defined as in the equation (2). Characters x' and y' denote the respective s-direction gradients, assuming that the beam traveling direction at the particle position (x, y) is the s axis. The left-hand side of the equation (2) denotes the particle position (x, y) at the isocenter, the s-direction gradients (x', y') at this particle position, and the momentum spread Δp/p$_0$. The right-hand side of the equation (2) denotes a transfer matrix M, the particle position (x, y) at the inlet of the gantry, the s-direction gradients (x', y') at this particle position, and the momentum spread Δp/p$_0$.

$$\begin{pmatrix} x \\ x' \\ y \\ y' \\ \frac{\Delta p}{p_0} \end{pmatrix}_{out} = \begin{pmatrix} r_{11} & r_{12} & r_{13} & r_{14} & r_{15} \\ r_{21} & r_{22} & r_{23} & r_{24} & r_{25} \\ r_{31} & r_{32} & r_{33} & r_{34} & r_{35} \\ r_{41} & r_{42} & r_{43} & r_{44} & r_{45} \\ 0 & 0 & 0 & 0 & 1 \end{pmatrix} \begin{pmatrix} x \\ x' \\ y \\ y' \\ \frac{\Delta p}{p_0} \end{pmatrix}_{in} = M \begin{pmatrix} x \\ x' \\ y \\ y' \\ \frac{\Delta p}{p_0} \end{pmatrix}_{in} \quad (2)$$

The transfer matrix M is a net transfer matrix determined by the values of the magnetic fields of the quadrupole electromagnets and the bending electromagnets provided in the beam transport line (that corresponds to the beam transport unit 15 of Embodiment 1) of the rotating gantry and the drift length. Here, the drift denotes a linear section (drift section) where no magnetic field exists; the drift length denotes the length of the linear section (drift section) where no magnetic field exists. Characters $r_{15}$, $r_{25}$, $r_{35}$, and $r_{45}$ denote the x-direction dispersion function ηx, the gradient ηx' of the dispersion function ηx, the y-direction dispersion function ηy, and the gradient ηy' of the dispersion function ηy, respectively.

Letting $M_n$ denote the transfer matrix of elements of a magnetic field or a drift, the net transfer matrix of the rotating gantry is given by the equation (3), when there exist n drifts.

$$M = M_n \ldots M_3 M_2 M_1 \quad (3)$$

In general, in the case of a rotating gantry in which the coupling between the respective motions of a particle in the x direction and the y direction is not utilized, the net transfer matrix of the gantry is given by the equation (4).

$$M = \begin{pmatrix} r_{11} & r_{12} & 0 & 0 & r_{15} \\ r_{21} & r_{22} & 0 & 0 & r_{25} \\ 0 & 0 & r_{33} & r_{34} & r_{35} \\ 0 & 0 & r_{43} & r_{44} & r_{45} \\ 0 & 0 & 0 & 0 & 1 \end{pmatrix} \quad (4)$$

As evident from the transfer matrix in the equation (4), each of the x component or the y component of a particle position, the s-direction gradient x' or y' at this particle position is obtained by adding three items; therefore, the motion of the particle is equivalent to that obtained by separately calculating the respective motions in the x direction and the y direction by use of "3×3" transfer matrix. In a conventional manner, in order to separately deal with the x-direction motion and the y-direction motion, i.e., in order not to consider the coupling between the x-direction particle motion and the y-direction particle motion, $r_{15}$ (the x-direction dispersion function ηx) of the transfer matrix M and $r_{35}$ (the y-direction dispersion function ηy) are set to "0", and the respective gradients $r_{25}$ (gradient ηx') and the $r_{45}$ (gradient ηy') of the s-direction dispersion functions ηx and ηx are also set to "0". This adjustment is performed by adjusting the values of the magnetic-field intensities of a plurality of quadrupole electromagnets. Originally, a two-pole electromagnet has the objective to lead a charged particle beam to the isocenter, the bending angle thereof is preliminarily determined, and the value of the magnetic field of the two-pole electromagnet is preliminarily determined; thus, the dispersion functions ηx and ηy and their gradients ηx' and ηy' cannot be adjusted by changing the value of the magnetic field of the two-pole electromagnet. Unlike a two-pole electromagnet, a quadrupole electromagnet has the objective to focus or defocus a charged particle beam; however, because the value of the magnetic field of the quadrupole electromagnet is not uniquely determined, the magnetic field of the quadrupole electromagnet is an adjustment parameter for adjusting the dispersion functions ηx and ηy and their gradients ηx' and ηy'.

As described above, to date, in order to sufficiently diminish the x-direction dispersion function η(ηx) that is caused by the magnetic field of the bending electromagnet and the s-direction gradient η'(ηx') of the dispersion function η, it has been required to provide at least one more bending electromagnet, the bending plane of which is on the same plane. Even if a quadrupole electromagnet is added, this addition alone cannot nullify both η and η'; thus, one more bending electromagnet is required. This applies to the y direction. With regard to the variation of the transfer matrix caused by the rotation of a rotating gantry, the mode of an incident beam that enter the rotating gantry is set in such a way that ηx=0, ηy=0, ηx'=0, and ηy'=0; then, if the mode in which ηx=0, ηy=0, ηx'=0, and ηy'=0 is established at the isocenter of a given rotation angle, the mode in which ηx=0, ηy=0, ηx'=0, and ηy'=0 is established at any other rotation angle.

However, as described above, in a conventional beam transport line where there exists no coupling between the x-direction particle motion and the y-direction particle motion, there exists only two cases, i.e., the case where the number of the bending planes of the bending electromagnets is one and the case where the bending planes are perpendicular to each other. In contrast to a conventional beam transport line, in the arrangement condition for the bending electromagnet 6 in the beam transport unit 15 of Embodiment 1, there exists no restriction on the foregoing bending plane; therefore, the degree of freedom in the designing is high. For example, in the case where the arrangement condition for the second bending electromagnet 6b is set in such a way that the bending plane of the bending electromagnet 6b is not on the same plane as the bending plane of the first bending electromagnet 6a, not parallel with the bending plane of the first bending electromagnet 6a, or not perpendicular to the bending plane of the first bending electromagnet 6a, the magnetic field thereof is exerted in both the x direction and the y direction; thus, regardless of the rotation angle of the rotating gantry, the transfer matrix M is given by the equation (5). The transfer matrix of the second bending electromagnet 6b is expressed as $M_2$.

$$M_2 = \begin{pmatrix} r_{11} & r_{12} & r_{13} & r_{14} & r_{15} \\ r_{21} & r_{22} & r_{23} & r_{24} & r_{25} \\ r_{31} & r_{32} & r_{33} & r_{34} & r_{35} \\ r_{41} & r_{42} & r_{43} & r_{44} & r_{45} \\ 0 & 0 & 0 & 0 & 1 \end{pmatrix} \quad (5)$$

Accordingly, even when the magnetic fields of the following bending electromagnet 6 and the quadrupole electromagnets 5 are arranged under the condition that the magnetic fields are exerted in only one of the x direction and the y direction, i.e., even when as a single element, the transfer matrix is defined as in the right-hand term of the equation (4), the net transfer matrix M of the overall beam transport unit 15 undergoes the effect of the transfer matrix $M_2$ of the second bending electromagnet 6b; therefore, each of $r_{15}$, $r_{25}$, $r_{35}$, and $r_{45}$ of the overall net transfer matrix M undergoes correlation components, i.e., other-direction components, in addition to the independent component in the x direction or the y direction.

Let's take advantage of the above fact; each of $r_{15}$, $r_{25}$, $r_{35}$, and $r_{45}$ of the overall net transfer matrix M undergoes correlation components, i.e., other-direction components; thus, when the arrangement positions of, the number of, and the magnetic-field values of a plurality of quadrupole electromagnets are appropriately adjusted, the values of $r_{15}$, $r_{25}$, $r_{35}$, and $r_{45}$, i.e., the dispersion functions ηx ($r_{15}$) and ηy ($r_{35}$) and their gradients ηx' ($r_{25}$) and ηy' ($r_{45}$) can be nullified or sufficiently be diminished. Therefore, it is not required that in order to nullify or sufficiently diminish each of $r_{15}$, $r_{25}$, $r_{35}$, and $r_{45}$ of the overall net transfer matrix M, two bending electromagnets are arranged in such a way that the bending planes thereof are the same. In other words, unlike Patent Documents 1 and 4, it is not required that the bending electromagnet at the downstream side is disposed in such a way that the bending plane thereof is the same as the bending plane of the bending electromagnet at the upstream side.

When the arrangement positions of, the number of, and the magnetic-field values of a plurality of quadrupole electromagnets are adjusted, the dispersion functions ηx and ηy and their gradients ηx' and ηy' can be nullified or sufficiently be diminished at the outlet of the beam transport unit 15 and at the isocenter, even in the case of such a particle beam rotational irradiation apparatus in which the beam path of the beam transport unit 15 is twisted, i.e., even in the case of the particle beam rotational irradiation apparatus 20 as described in Embodiment 1; therefore, it is made possible to diminish the momentum-spread dependency of a beam width, i.e., the momentum spread $\Delta p/p_0$ can be cancelled to the extent that its contribution to the beam width is sufficiently small. Mathematically, the desired solution for nullifying or sufficiently diminishing the four components $r_{15}$, $r_{25}$, $r_{35}$, and $r_{45}$ in the elements of the matrix exists at a high probability. It goes without saying that when the number of provided quadrupole electromagnets is more than 4, the adjustment is facilitated.

Figure 4:
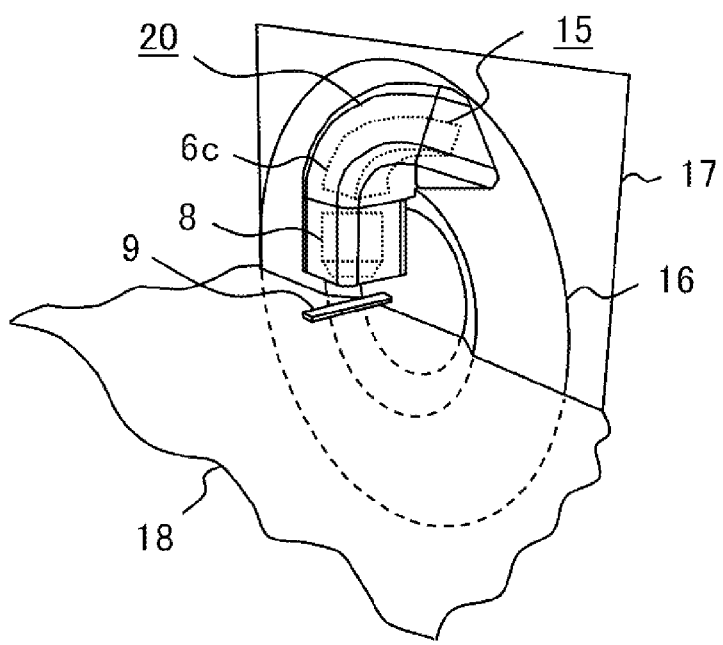
FIG. 4 is a perspective view of the particle beam rotational irradiation apparatus in FIG. 1, taken from the irradiation room.

Moreover, the particle beam rotational irradiation apparatus can be realized with three bending electromagnets, while four bending electromagnets are required for a corkscrew-type. Still moreover, in the case where as illustrated in FIG. 4, the particle beam rotational irradiation apparatus 20 is installed in such a way that the front end of the irradiation nozzle 8 protrudes toward the irradiation room, it is made possible to realize a small-size and open-type rotating gantry. FIG. 4 is a perspective view of the particle beam rotational irradiation apparatus in FIG. 1, taken from the irradiation room. A rotation front cover 16 is a cover mounted on the rotating unit 1 in such a way as to cover the front side of the rotating unit 1 and rotates as the rotating unit 1 rotates. The rotation front cover 16 is disposed in a rotatable manner in the through-hole opened in an irradiation room wall 17. The particle beam rotational irradiation apparatus 20 according to Embodiment 1 is an open-type rotating gantry and is characterized in that the last bending electromagnet 6c is disposed obliquely with respect to the irradiation room wall 17. The particle beam rotational irradiation apparatus 20 according to Embodiment 1 is an open-type rotating gantry in which a treatment table 9 can be disposed on an irradiation room base 18; therefore, unlike such a particle beam rotational irradiation apparatus in which the treatment table 9 is disposed in the narrow inner chamber of the rotating gantry, the particle beam rotational irradiation apparatus 20 can facilitate patient positioning work and hence the throughput of the particle beam therapy is raised.

In Embodiment 1, as can be seen from FIG. 3, the beam transport unit 15 is configured in such a way that the respective bending planes of the bending electromagnets 6a, 6b, and 6c are not on the same plane, not parallel with one another, and not perpendicular to one another. The respective magnetic fields of the quadrupole electromagnets 5a, 5b, 5c, and 5d of the beam transport unit 15 are set in such a way that the beam width (beam size) of the charged particle beam 14 at the outlet of the beam transport unit 15, i.e., at the outlet of the downstreammost bending electromagnet 6c falls within the tolerance range, i.e., in such a way that the dispersion functions $\eta x$ and $\eta y$ of the charged particle beam 14 and their gradients $\eta x'$ and $\eta y'$ are nullified or sufficiently diminished at the outlet of the bending electromagnet 6c. In the particle beam rotational irradiation apparatus 20 according to Embodiment 1, the beam transport unit 15 is configured in such a way that the respective bending planes of the bending electromagnets 6a, 6b, and 6c are not on the same plane, not parallel with one another, and not perpendicular to one another, and the respective magnetic fields of the quadrupole electromagnets 5a, 5b, 5c, and 5d of the beam transport unit 15 are set in such a way that the dispersion functions $\eta x$ and $\eta y$ of the charged particle beam 14 and their gradients $\eta x'$ and $\eta y'$ are nullified or sufficiently diminished at the outlet of the downstreammost bending electromagnet 6c; therefore, the small-size and open-type particle beam rotational irradiation apparatus 20 can be realized.

Not only in the case where the beam transport unit 15 is configured in such a way that the respective bending planes of the bending electromagnets 6a, 6b, and 6c are not on the same plane, not parallel with one another, and not perpendicular to one another, but also in the case where the three bending electromagnets 6a, 6b, and 6c are arranged in such a way that the bending planes of at least one pair among three pairs of the bending planes thereof are not on the same plane, not parallel with each other, and not perpendicular to each other, the foregoing explanation is established, because regardless of how to set the x axis and the y axis, the magnetic fields are exerted in such a way that the motions of a particle in the x direction and the y direction are coupled with each other, i.e., any one of the transfer matrix $M_n$ is given by the equation (5). Therefore, in this case, as well, the respective magnetic fields of the quadrupole electromagnets 5a, 5b, 5c, and 5d of the beam transport unit 15 are set in such a way that the dispersion functions $\eta x$ and $\eta y$ of the charged particle beam 14 and their gradients $\eta x'$ and $\eta y'$ are nullified or sufficiently diminished at the outlet of the beam transport unit 15, i.e., at the outlet of the downstreammost bending electromagnet 6c; thus, the small-size and open-type particle beam rotational irradiation apparatus 20 can be realized.

However, as a matter of course, the relationship in which the respective bending planes of the bending electromagnets 6a, 6b, and 6c are not on the same plane, not parallel with one another, or not perpendicular to one another raises, compared with the other manner, the degree of freedom in adjusting the magnetic fields of the quadrupole electromagnets 5a, 5b, 5c, and 5d and hence facilitates obtaining desired beam parameters (a beam size and a gradient with respect to the beam traveling direction (the beam center axis)). Moreover, by utilizing three bending electromagnets, the number of the bending electromagnets can be minimized compared with the case where four bending electromagnets are utilized; thus, the low-cost particle beam rotational irradiation apparatus 20 can be realized. Still moreover, as the bending electromagnet 6, a bending electromagnet in which four-pole components including the magnetic field at the end are utilized is adopted so as to replace part of the quadrupole electromagnets 5 and to decrease the number of the quadrupole electromagnets 5, so that the cost can be reduced.

As described above, the particle beam rotational irradiation apparatus 20 according to Embodiment 1 is provided with the irradiation nozzle 8 that irradiates the charged particle beam 14, the beam transport unit 15 that transports the charged particle beam 14 to the irradiation nozzle 8, and the rotating unit 1 that can rotate around the isocenter; the beam transport unit 15 has three or more bending electromagnets 6. The bending electromagnets 6a, 6b, and 6c are arranged in such a way that in the case where as a pair of bending planes, any two of the bending planes of the bending electromagnets 6 are selected, the two bending planes of at least one pair of bending planes are not on the same plane, not parallel with each other, and not perpendicular to each other; therefore, the respective motions of a charged particle in the x direction and the y direction are coupled with each other; thus, because it is not required to perform the adjustment both in the x direction and in the y direction, the working space for performing patient positioning work can be widened even in the case of a small-size particle beam rotational irradiation apparatus and hence the throughput of particle beam therapy can be improved.

Embodiment 2

Figure 5:
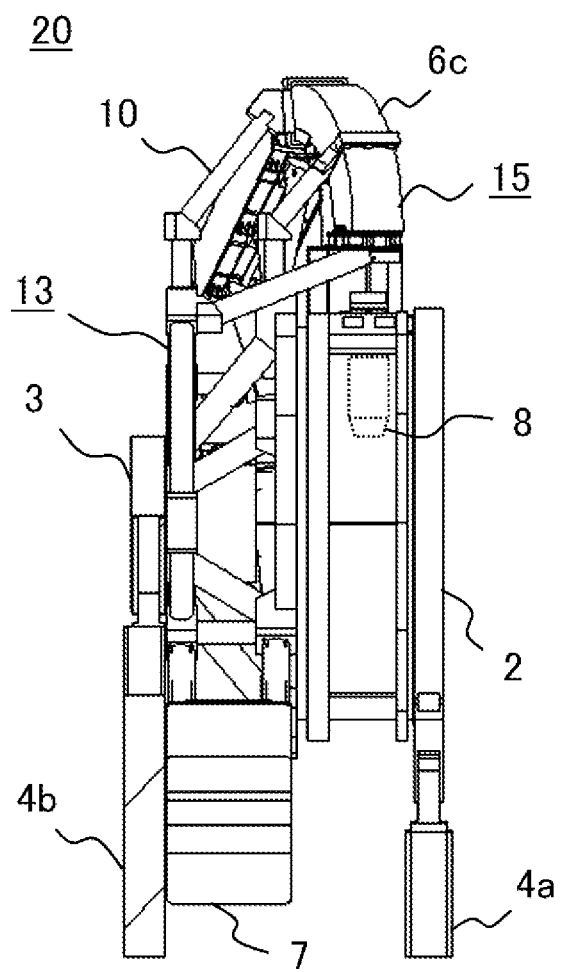
FIG. 5 is a side view illustrating a particle beam rotational irradiation apparatus according to Embodiment 2 of the present invention.
Figure 6:
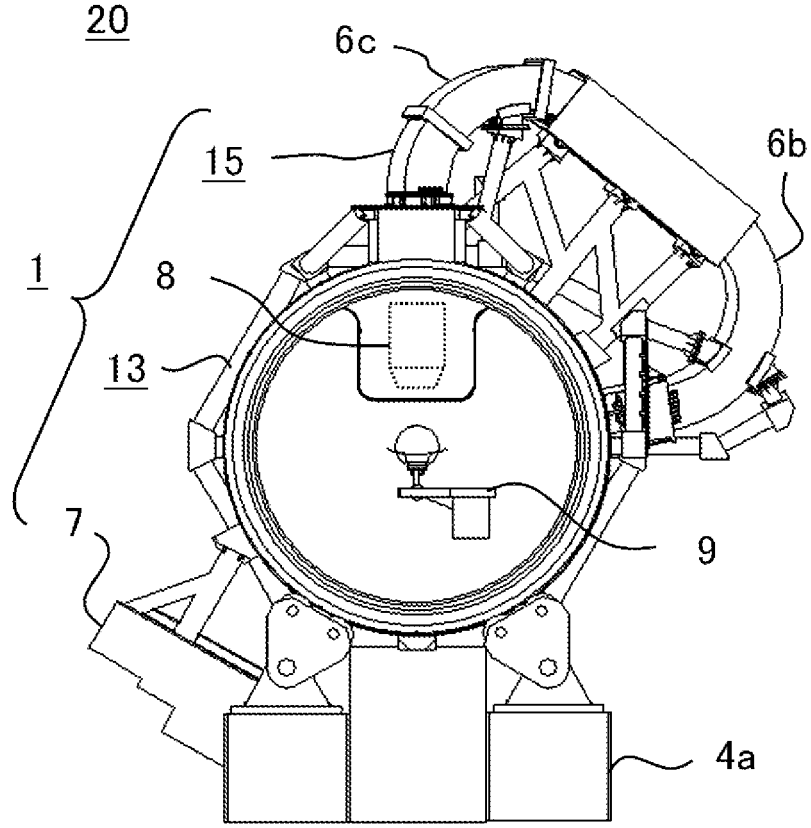
FIG. 6 is an elevation view illustrating the particle beam rotational irradiation apparatus in FIG. 5.

FIG. 5 is a side view illustrating a particle beam rotational irradiation apparatus according to Embodiment 2 of the present invention; FIG. 6 is an elevation view illustrating a particle beam rotational irradiation apparatus according to Embodiment 2 of the present invention. A particle beam irradiation apparatus 20 according to Embodiment 2 has a structure that is not an open type. Because the last two bending electromagnets 6b and 6c are not arranged in a row, the width of an inner chamber, which is a tunnel portion in which a patient who undergoes a therapy is situated, can be enlarged in comparison with a particle beam rotational irradiation apparatus according to Patent Document 1 or 4; thus, a relatively open rotating gantry can be realized. Because being not an open type, the particle beam rotational irradiation apparatus 20 according to Embodiment 2 has an advantage that in comparison to the particle beam rotational irradiation apparatus 20 according to Embodiment 1, the irradiation nozzle 8 can readily be supported.

Because in the particle beam rotational irradiation apparatus 20 according to Embodiment 2, the width of an inner chamber, which is a tunnel portion in which a patient who undergoes a therapy is situated, can be enlarged in comparison with a particle beam rotational irradiation apparatus according to Patent Document 1 or 4, a relatively open rotating gantry can be realized; thus, there can be realized a particle beam rotational irradiation apparatus that can raise the throughput of particle beam therapy and is downsized. Even though being a small-size particle beam rotational irradiation apparatus, the particle beam rotational irradiation apparatus 20 according to Embodiment 2 makes it possible to widen the working space where work in the vicinity of the irradiation nozzle 8 is performed and hence the throughput of particle beam therapy can be improved. Moreover, a monitoring apparatus provided utilizing the wide space facilitates irradiation while performing moving body tracking.

Embodiment 3

In Embodiment 1, it has been explained that when the arrangement positions of, the number of, and the magnetic-field values of a plurality of quadrupole electromagnets are adjusted, the dispersion functions ηx and ηy and their gradients ηx' and ηy' can be nullified or sufficiently be diminished at the outlet of the beam transport unit 15 and at the isocenter, even in the case of a particle beam rotational irradiation apparatus in which the beam path of the beam transport unit 15 is twisted, i.e., even in the case of the particle beam rotational irradiation apparatus 20 as described in Embodiment 1, and hence the momentum-spread dependence of a beam width can be diminished. In Embodiment 3, it will be explained that by contriving the arrangement positions of the magnetic poles of the quadrupole electromagnets 5, it is made possible to transport a beam having no xy correlation at the isocenter.

Figure 7:
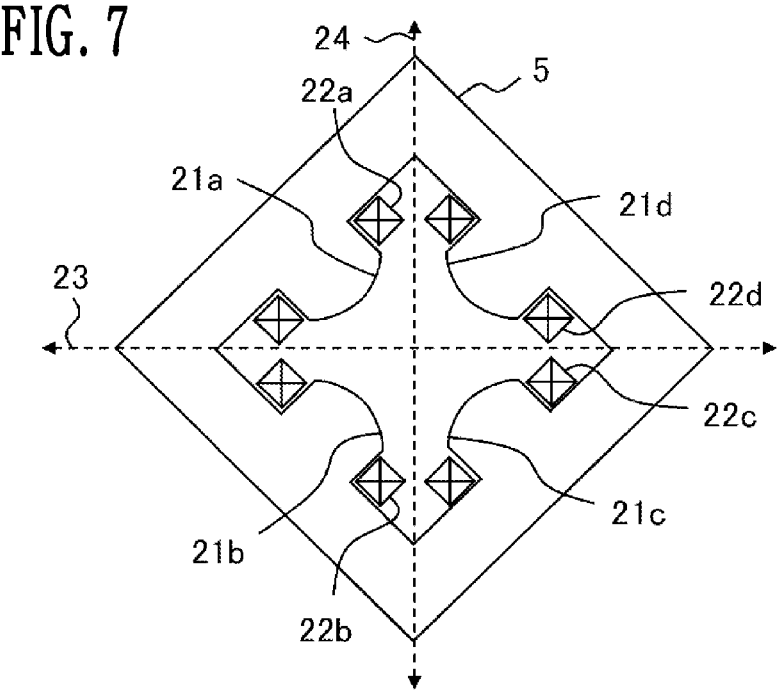
FIG. 7 is a diagram for explaining the acting direction of a quadrupole electromagnet of the present invention.
Figure 9:
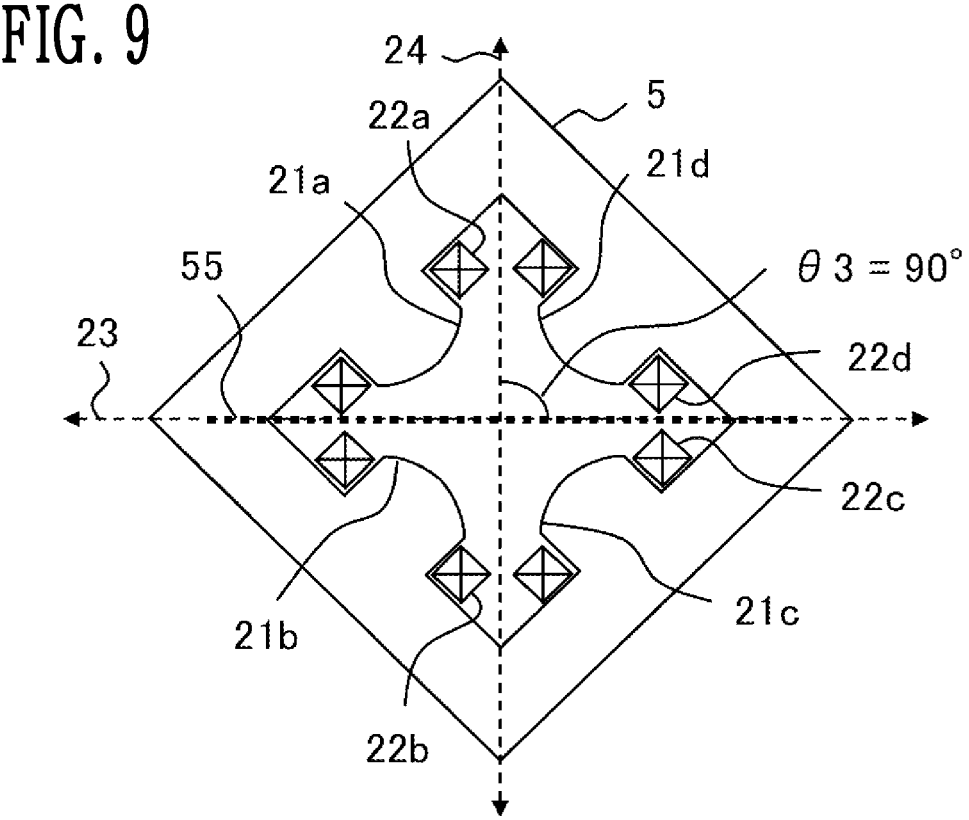
FIG. 9 is a diagram illustrating the arrangement of the acting directions of the magnetic poles in a conventional quadrupole electromagnet.

At first, the relationship between the magnetic pole 21 of the quadrupole electromagnet 5 and the focusing or defocusing direction of the charged particle beam 14 will be explained. FIG. 7 is a diagram for explaining the acting direction of a quadrupole electromagnet of the present invention. The quadrupole electromagnet 5 is an electromagnet having four magnetic poles 21a, 21b, 21c, and 21d and coils 22a, 22b, 22c, and 22d wound around those magnetic poles; these magnetic poles and coils focus or defocus the charged particle beam 14 in the broken-line arrow 23 or 24. The direction from the center to the outside is a defocusing direction, and the direction from the outside to the center is a focusing direction. The directions of the broken-line arrows 23 and 24 will be referred to as acting directions 23 and 24 in each of which focusing and defocusing occurs. In general, in a conventional beam transport line, the quadrupole electromagnet 5 is disposed in such a way that the acting directions 23 and 24 are each perpendicular to or parallel with the bending plane of the bending electromagnet 6 and is utilized in such a way that the x-direction motion and the y-direction motion of a particle are not coupled with each other. In other words, the quadrupole electromagnet 5 in a conventional beam transport line is disposed in such a way that as illustrated in FIG. 9, the bending plane 55 of the bending electromagnet 6 is parallel with the acting direction 23 and perpendicular to the acting direction 24. FIG. 9 is a diagram illustrating the arrangement of the acting directions of the magnetic poles in a conventional quadrupole electromagnet.

Next, there will be explained how to deal with a beam in a rotating gantry. The post-drift positions and the gradients of the traveling directions of respective charged particles that form a beam are determined by the equation (2); however, the parameters (the beam size, the beam gradient with respect to the beam traveling direction (beam center-axis direction) of a beam, which is an aggregate of charged particles, can be described by a σ matrix, which is a statistic quantity of the particle distribution, and is given by the equation (6).

$$\sigma = \begin{pmatrix} \sigma_{11} & \sigma_{12} & \sigma_{13} & \sigma_{14} \\ \sigma_{21} & \sigma_{22} & \sigma_{23} & \sigma_{24} \\ \sigma_{31} & \sigma_{32} & \sigma_{33} & \sigma_{34} \\ \sigma_{41} & \sigma_{42} & \sigma_{43} & \sigma_{44} \end{pmatrix} = \begin{pmatrix} \langle x^2 \rangle & \langle xx' \rangle & \langle xy \rangle & \langle xy' \rangle \\ \langle xx' \rangle & \langle x'^2 \rangle & \langle x'y \rangle & \langle x'y' \rangle \\ \langle xy \rangle & \langle x'y \rangle & \langle y^2 \rangle & \langle yy' \rangle \\ \langle xy' \rangle & \langle x'y' \rangle & \langle yy' \rangle & \langle y'^2 \rangle \end{pmatrix} \quad (6)$$

The relationship between the σ matrix and the transfer matrix M is given by the equation (7). The equation (7) is shown in a document (Jean Buon LAL/RT96-03 April 1996). In the case of rotating gantries disclosed in Patent Documents 1 through 4, by rotating the coordinate system along with the rotation of the rotating gantry, there can be designed the transport of a beam in which, ideally, there are no xy correlation components of the beam parameters (the beam size, the beam gradient with respect to the beam traveling direction (beam center-axis direction).

$$\sigma_2 = M\sigma_1 M^T \quad (7)$$

Figure 8:
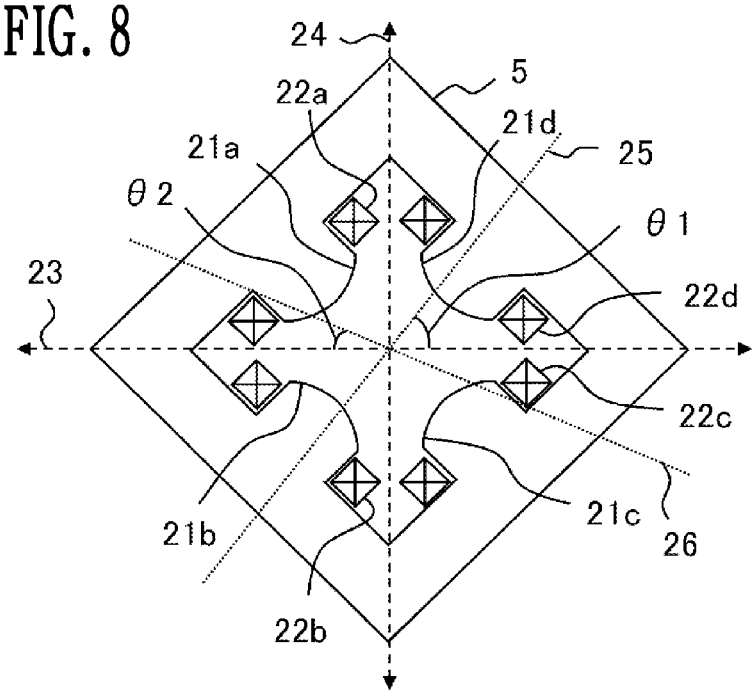
FIG. 8 is a diagram illustrating the arrangement of the acting directions of the magnetic poles in a quadrupole electromagnet according to Embodiment 3 of the present invention.
Figure 10:
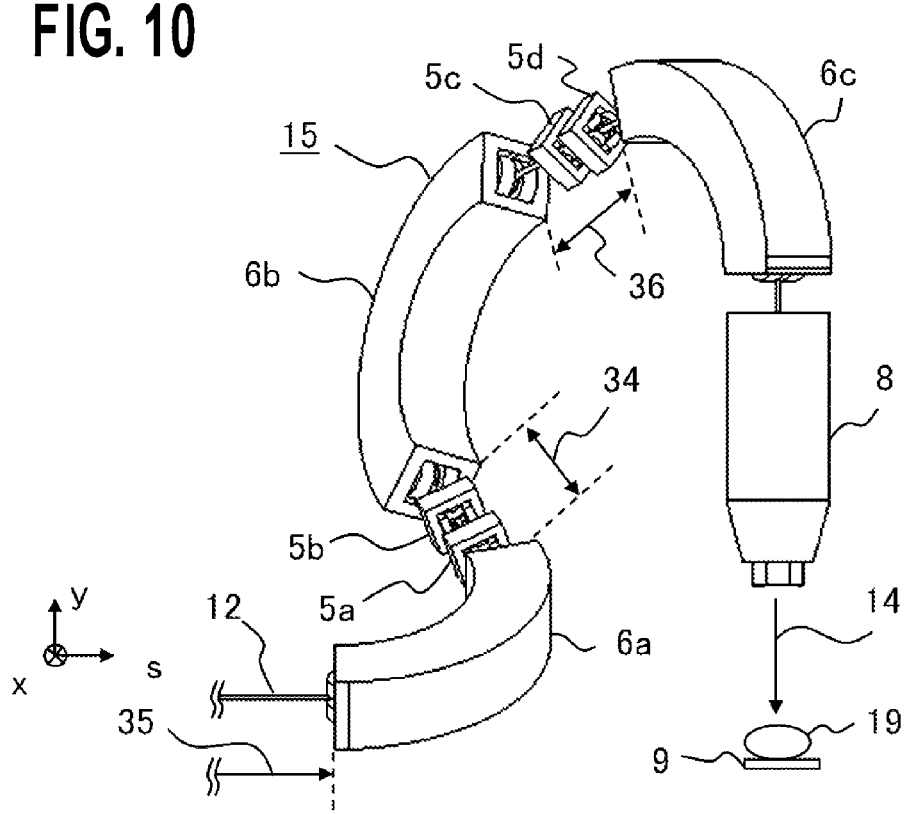
FIG. 10 is a diagram illustrating the mounting position of the quadrupole electromagnet in FIG. 8.

Next, there will be explained the arrangement of the positions of the magnetic poles in the foregoing quadrupole electromagnet 5. FIG. 8 is a diagram illustrating the arrangement of the acting directions of the magnetic poles in a quadrupole electromagnet according to Embodiment 3 of the present invention; FIG. 10 is a diagram illustrating the mounting position of the quadrupole electromagnet in FIG. 8. In the rotating gantry (particle beam rotational irradiation apparatus 20) according to the present invention, even when as the x axis and the y axis of the charged particle beam 14, whatever two axes that are perpendicular to each other are selected, the components ($r_{13}$, $r_{14}$, $r_{23}$, $r_{24}$, $r_{31}$, $r_{32}$, $r_{41}$, and $r_{42}$), in the transfer matrix M, that each generate the correlations between the x-direction particle motion and the y-direction particle motion do not become "0"; therefore, even when there exists no xy correlation in $\sigma_1$ (the spread of a beam launched into the gantry), the equation (7) suggests that the components ($\sigma_{13} = \sigma_{31}$, $\sigma_{14} = \sigma_{41}$, $\sigma_{23} = \sigma_{32}$, and $\sigma_{24} = \sigma_{42}$), in the beam parameters (the beam size, the beam gradient with respect to the beam traveling direction (the direction of the beam-center axis)) of $\sigma_2$ (the spread of a beam that exits from the gantry), that each indicate the xy correlations are not "0". In this case, when both the x-direction beam size (beam width) and the y-direction beam size of the charged particle beam 14 are reduced, especially in the section between the last bending electromagnet (the bending electromagnet 6c in FIG. 10) and the isocenter, one of the beam sizes or its gradient always provides an effect to the other direction; thus, the adjustment becomes difficult in both directions. Moreover, it is required to make a treatment plan for which a beam having the xy correlation is taken into consideration. That is to say, in the particle beam rotational irradiation apparatus 20 according to Embodiment 1, the foregoing problem is still remaining.

The foregoing problem does not exist in a conventional rotating gantry where as the x axis and the y axis of the charged particle beam 14, two axes, i.e., an axis that is horizontal to the bending plane of the bending electromagnet 6 and an axis that is vertical to the bending plane of the bending electromagnet 6 are selected, the σ matrix can be considered as a matrix where there exists no coupling, i.e., a matrix, the x direction and the y direction components of which are independent from each other in such a way that $\sigma_{13} = \sigma_{31} = 0$, $\sigma_{14} = \sigma_{41} = 0$, $\sigma_{23} = \sigma_{32} = 0$, and $\sigma_{24} = \sigma_{42} = 0$. Accordingly, as illustrated in FIG. 8, the quadrupole electromagnet 5 is disposed with its magnetic-pole positions arranged in such a way that the focusing direction and the defocusing direction thereof are neither parallel with nor perpendicular to the bending planes 25 and 26 of the bending electromagnets 6 situated at both sides thereof (at the immediate upstream side and the immediate downstream side of the quadrupole electromagnet 5). In the case where the quadrupole electromagnet 5 is disposed in this manner, the components that generate the particle-motion xy correlation in the transfer matrix M for the quadrupole electromagnet 5 are not "0" and hence act on the components, caused by the bending electromagnet disposed under the condition of the present invention, that generate the particle-motion xy correlation; therefore, the components that generate the particle-motion xy correlation can be reduced at the last bending electromagnet (the bending electromagnet 6c in FIG. 10) to the extent that the components ($\sigma_{13} = \sigma_{31}$, $\sigma_{14} = \sigma_{41}$, $\sigma_{23} = \sigma_{32}$, and $\sigma_{24} = \sigma_{42}$) is "0" or the effect on the beam size can sufficiently be neglected. FIG. 8 illustrates an example in which the angle between the bending plane 25 and the acting direction 23 is θ1 (0<θ1<90°) and the angle between the bending plane 26 and the acting direction 23 is θ2 (0<θ2<90°).

Figure 11:
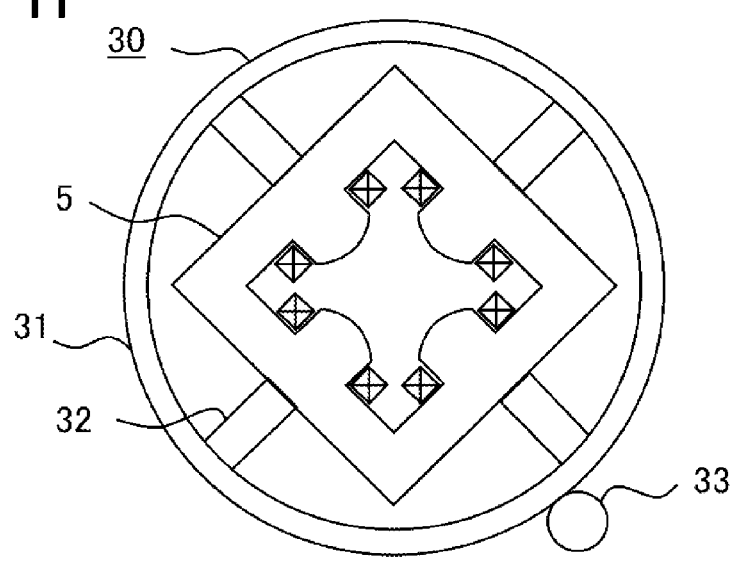
FIG. 11 is a diagram illustrating the rotation-driving mechanism of a quadrupole electromagnet according to Embodiment 3 of the present invention.

Moreover, in comparison with a conventional particle beam rotational irradiation apparatus in which only the magnetic-field intensity of the quadrupole electromagnet 5 and the arrangement position, on the beam path, of the quadrupole electromagnet 5 are dealt with as designing parameters, the particle beam rotational irradiation apparatus 20 according to Embodiment 3 makes it possible to perform the designing by use of the rotation angle (the angles θ1 and θ2 in FIG. 8) of the quadrupole electromagnet 5 with respect to the beam center, as adjustment parameters; therefore, the degree of freedom in the designing can be raised. Conventionally, the rotation angle of the quadrupole electromagnet 5 is 90° (θ3), as illustrated in FIG. 9, and does not work as an adjustment parameter. In the case where as illustrated in FIG. 11, a rotation-driving mechanism 30 capable of driving the quadrupole electromagnet 5 in a rotating manner is provided, the rotation angle θ of the quadrupole electromagnet 5 can be adjusted even when due to a magnetic-field error or the like, the beam size differs from the designed beam size; thus, it can be expected that the degree of freedom in the adjustment of the beam size is raised. FIG. 11 is a diagram illustrating the rotation-driving mechanism of a quadrupole electromagnet according to Embodiment 3 of the present invention. The rotation-driving mechanism 30 is provided with a ring 31, a supporting member 32 that connects the quadrupole electromagnet 5 with the ring 31, and a rotation-driving device 33 that makes the ring 31 rotate.

In general, in the beam transport line, various adjustment methods are utilized for the purpose of correcting the fact that due to the effect of a magnetic-field error, the beam orbit center differs from the designed beam orbit center. For example, the orbit correction (a defocused orbit center is corrected to be the designed orbit center) through a method in which a steering electromagnet (two-pole electromagnet) is disposed in the beam transport line and is energized, a method in which an auxiliary coil is wound around the bending electromagnet 6 in the beam transport line and is energized by a current, a method in which as an offset, a current corresponding to a magnet field required for the orbit correction is made to flow in the bending electromagnet 6 of the beam transport line, and the like. In general, when the x-direction and y-direction beam parameters (the beam size, the beam gradient with respect to the beam traveling direction (the direction of the beam-center axis)) are not coupled with each other, the orbit correction is performed in both the x axis and the y axis; in order to implement this, a magnet for exerting a magnetic field in the x direction and a magnet for exerting a magnetic field in the y direction are required (in some cases, a single magnet, which generates two-pole magnetic field in the both directions, is utilized).

In some cases, the foregoing method is utilized also in the particle beam rotational irradiation apparatus 20 according to the present invention; however, in that case, even when the foregoing correction method is utilized at the place where there exists the xy correlation, the xy correlation provides an effect to not only the y-direction beam but also the x-direction beam when a magnetic field is exerted in the x direction; therefore, in some cases, the adjustment time becomes long. In particular, because the charged particle beam 14 launched from the irradiation nozzle 8 is a beam that is immediately utilized in the therapy, it is desired that the xy correlation in the charged particle beam 14 is sufficiently diminished and then the orbit thereof is corrected. Accordingly, after the correlation between the axis that is vertical to the bending plane of the last bending electromagnet (the bending electromagnet 6c in FIG. 10) and the axis that is horizontal to the bending plane of the last bending electromagnet is cancelled by the second-from-the-last bending electromagnet (the bending electromagnet 6b in FIG. 10), a steering electromagnet is disposed in a setting section (between the second-from-the-upstream-side bending electromagnet 6b and the third-from-the-upstream-side bending electromagnet 6c) so that the orbit correction can be performed separately in the both axes; as a result, the orbit of the charged particle beam 14 can readily be corrected.

In this case, the quadrupole electromagnets 5 having the magnetic-pole arrangement illustrated in FIG. 8 are disposed before the second-from-the-last bending electromagnet (the bending electromagnet 6b in FIG. 10); for example, in the case where as illustrated in FIG. 10, the gantry has three bending electromagnets 6, the quadrupole electromagnets 5 are disposed in a setting section 34 between the first-from-the-upstream-side bending electromagnet 6a and the second-from-the-upstream-side bending electromagnet 6b, in a setting section 35 before the first-from-the-upstream-side bending electromagnet 6a, or in both the setting section 34 and the setting section 35. The quadrupole electromagnet 5 having the magnetic-pole arrangement illustrated in FIG. 8 also rotates along with the rotating gantry, while maintaining the relative position between the rotating gantry and itself.

In the particle beam rotational irradiation apparatus 20 according to Embodiment 3, at least one quadrupole electromagnet 5 is disposed in the beam transport unit 15 in such a way that the focusing direction and the defocusing direction thereof are neither parallel with nor perpendicular to the respective bending planes 25 and 26 of the bending electromagnets 6 situated at both sides thereof (at the immediate upstream side and the immediate downstream side thereof); therefore, it is made possible to transport the charged particle beam 14 having no xy correlation to the isocenter. Moreover, in the particle beam rotational irradiation apparatus 20 according to Embodiment 3, the quadrupole electromagnets 5 is disposed in the drift section (the setting section 34 or 35) before the second-from-the-last bending electromagnet (the bending electromagnet 6b in FIG. 10) in the beam transport unit 15 in such a way that the focusing direction and the defocusing direction thereof are neither parallel with nor perpendicular to the respective bending planes 25 and 26 of the bending electromagnets 6 situated at both sides thereof (at the immediate upstream side and the immediate downstream side thereof); therefore, it is made possible to transport the charged particle beam 14 having no xy correlation to the isocenter and to readily correct the orbit of the beam.

Next, the installation of an irradiation-field-enlargement electromagnet or a scanning electromagnet will be described. In the case where the last bending electromagnet 6c cancels the xy correlation, a pair of irradiation-field-enlargement electromagnets (e.g., Wobbler electromagnets) for enlarging a beam or a pair of scanning electromagnet for scanning a beam is disposed in a section from the last bending electromagnet 6c to the isocenter, i.e., in the irradiation nozzle 8. In the case where in this situation, the x axis and the y axis of the charged particle bean 14 are an axis that is perpendicular to the bending plane of the last bending electromagnet 6c and an axis that is parallel with the bending plane of the last bending electromagnet 6c, the condition in which there exists no xy correlation is maintained during the therapy, when the foregoing irradiation-field-enlargement electromagnet or scanning electromagnet is disposed in such a way that the bending plane thereof is perpendicular to or parallel with the bending plane of the last bending electromagnet 6c; therefore, it is not required to make a treatment plan for which the xy correlation is taken into consideration, and hence it can be expected that the time for making the treatment plan is shortened.

In the particle beam rotational irradiation apparatus 20 according to Embodiment 3, the irradiation-field-enlargement electromagnet or the scanning electromagnet, which is disposed in a section from the last bending electromagnet 6c in the beam transport unit 15 to the isocenter, is provided in such a way that the direction of the two-pole magnetic field thereof is parallel with or perpendicular to the direction of the magnetic field of the last bending electromagnet 6c; therefore, it is made possible to transport the charged particle beam 14 having no xy correlation to the isocenter and to readily adjust the beam size at the isocenter and the beam center position.

Furthermore, in the case where the correlation between the x-direction particle motion and the y-direction particle motion can sufficiently be diminished only by disposing at least one quadrupole electromagnet which is made in such a way that the focusing direction and the defocusing direction thereof are neither parallel with nor perpendicular to the respective bending planes of the bending electromagnets situated at both sides thereof in a drift section before the second-from-the-last bending electromagnet (the bending electromagnet 6b in FIG. 10), the xy correlation of the beam in the setting section 36 has already been cancelled (in the direction of the magnetic field of the last bending electromagnet 6c); therefore, it is made possible to dispose an irradiation-field-enlargement electromagnet or a scanning electromagnet in the setting section 36. As a result, the irradiation nozzle 8 is downsized, and hence it can be expected that the rotation diameter of the gantry is diminished.

The orbit correction is performed with a two-pole electromagnet; therefore, a pair of beam scanning electromagnets (scanning electromagnets) or irradiation-field-enlargement electromagnets (Wobbler electromagnets) that scans a beam in two vertical-axis directions is disposed in a section between the second-from-the-last bending electromagnet 6b and the last bending electromagnet 6c and then an auxiliary coil is wound around the magnet of at least one of the beam scanning electromagnet or the irradiation-field-enlargement electromagnet or offset current energization is performed, so that the orbit correction in which no xy coupling occurs can also be performed. In this situation, the beam scanning electromagnet or the irradiation-field-enlargement electromagnet is disposed in such a way that the direction of the two-pole magnetic field is horizontal or vertical to the bending plane of the last bending electromagnet 6c. In this case, the arrangement from the irradiation nozzle 8 is changed, and the beam scanning electromagnet or the irradiation-field-enlargement electromagnet is integrated in the beam transport unit 15.

In another particle beam rotational irradiation apparatus 20 according to Embodiment 3, the beam scanning electromagnet or the irradiation-field-enlargement electromagnet is disposed in a section between the last bending electromagnet 6c in the beam transport unit 15 and the second-from-the last bending electromagnet 6b is provided in such a way that the direction of the two-pole magnetic field thereof is parallel with or perpendicular to the direction of the magnetic field of the last bending electromagnet 6c; therefore, it is made possible to transport the charged particle beam 14 having no xy correlation to the isocenter and to readily correct orbit-center displacement caused by a magnetic-field error. Moreover, another particle beam rotational irradiation apparatus 20 according to Embodiment 3 is configures in such a manner as described above; therefore, because the beam scanning electromagnet or the irradiation-field-enlargement electromagnet can have a function as a steering magnet, the number of the steering magnets can be reduced.

Various modifications and alterations of this invention will be apparent to those skilled in the art without departing from the scope and spirit of this invention, and it should be understood that this is not limited to the illustrative embodiments set forth herein.

What is claimed is:

1. A particle beam rotational irradiation apparatus that irradiates a charged particle beam, accelerated by an accelerator, from an arbitrary angle direction with respect to an isocenter, the particle beam rotational irradiation apparatus comprising:
    an irradiation nozzle that irradiates the charged particle beam;
    a beam transport unit that transports the charged particle beam to the irradiation nozzle; and
    a rotating unit that can rotate around the isocenter,
    wherein the beam transport unit has three or more bending electromagnets, and
    wherein the bending electromagnets are arranged in such a way that in the case where as a pair of bending planes, any two of the bending planes of the bending electromagnets are selected, the two bending planes of at least one pair of bending planes are not on the same plane, not parallel with each other, and not perpendicular to each other.

2. The particle beam rotational irradiation apparatus according to claim 1, wherein the bending electromagnets are arranged in the beam transport unit in such a way that in the case where as a pair of bending planes, any two of the bending planes of the bending electromagnets are selected, the two bending planes of any pair of bending planes are not on the same plane, not parallel with each other, and not perpendicular to each other.

3. The particle beam rotational irradiation apparatus according to claim 1, wherein in the beam transport unit, the magnetic fields of the bending electromagnets are set in such a way that the value of a dispersion function of the charged particle beam at the outlet of the beam transport unit and the value of the gradient of the dispersion function with respect to the traveling direction of the charged particle beam are set as the beam width of the charged particle beam at the isocenter falls with a tolerance range.

4. The particle beam rotational irradiation apparatus according to claim 1, wherein the beam transport unit has three of the bending electromagnets.

5. The particle beam rotational irradiation apparatus according to claim 1,
    wherein in the beam transport unit, the bending electromagnet at the downstreammost side thereof is disposed obliquely with respect to the wall of an irradiation room, and
    wherein the irradiation nozzle is disposed inside the irradiation room.

6. The particle beam rotational irradiation apparatus according to claim 1, wherein in the beam transport unit, two of the bending electromagnets that are first and second from the downstreammost side thereof are arranged in such a way that the plane including the line connecting the respective centers of the two bending electromagnets and the isocenter is oblique to the rotation axis of the rotating unit.

7. The particle beam rotational irradiation apparatus according to claim 1, wherein the beam transport unit has at least one quadrupole electromagnet in which the acting directions of focusing and defocusing of the charged particle beam are neither parallel with nor perpendicular to the respective bending planes of the bending electromagnets situated at the immediate upstream side and the immediate downstream side thereof.

8. The particle beam rotational irradiation apparatus according to claim 1, wherein in a drift section before the bending electromagnet that is the second from the downstreammost side thereof, the beam transport unit has at least one quadrupole electromagnet in which the acting directions of focusing and defocusing of the charged particle beam are neither parallel with nor perpendicular to the respective bending planes of the bending electromagnets situated at the immediate upstream side and the immediate downstream side thereof.

9. The particle beam rotational irradiation apparatus according to claim 1,
wherein the irradiation nozzle has a set of at least two irradiation-field-enlargement electromagnets for enlarging the irradiation field of the charged particle beam or a set of at least two scanning electromagnets for scanning the charged particle beam, and
wherein the irradiation-field-enlargements electromagnets or the scanning electromagnets are arranged in such a way that the direction of the two-pole magnetic field thereof is parallel with or perpendicular to the direction of the magnetic field of the bending electromagnet situated at the downstreammost side in the beam transport unit.

10. The particle beam rotational irradiation apparatus according to claim 1,
wherein in a section between the bending electromagnet at its downstreammost side and the bending electromagnet that is the second from its downstreammost side, the beam transport unit has a set of at least two irradiation-field-enlargement electromagnets for enlarging the irradiation field of the charged particle beam or a set of at least two scanning electromagnets for scanning the charged particle beam, and
wherein the irradiation-field-enlargements electromagnets or the scanning electromagnets are arranged in such a way that the direction of the two-pole magnetic field thereof is parallel with or perpendicular to the direction of the magnetic field of the bending electromagnet situated at the downstreammost side in the beam transport unit.

* * * * *